US00PP29680P3

(12) United States Plant Patent
van Heesbeen

(10) Patent No.: US PP29,680 P3
(45) Date of Patent: Sep. 18, 2018

(54) ***EUONYMUS* PLANT NAMED 'HEESMIK'**

(50) Latin Name: *Euonymus japonicus*
Varietal Denomination: HEESMIK

(71) Applicant: Van Heesbeen Cultures B.V., Rijsbergen (NL)

(72) Inventor: Ad van Heesbeen, Rijsbergen (NL)

(73) Assignee: Van Heesbeen Cultures B.V., Rijsbergen (NL)

( * ) Notice: Subject to any disclaimer, the term of this patent is extended or adjusted under 35 U.S.C. 154(b) by 0 days.

(21) Appl. No.: 15/732,265

(22) Filed: Oct. 17, 2017

(65) Prior Publication Data

US 2018/0110166 P1 Apr. 19, 2018

(30) Foreign Application Priority Data

Oct. 18, 2016 (QZ) ..... PBR 2016/2529

(51) Int. Cl.
*A01H 5/00* (2018.01)
*A01H 5/02* (2018.01)
*A01H 5/12* (2018.01)

(52) U.S. Cl.
USPC ..... Plt./246
CPC ..... *A01H 5/02* (2013.01); *A01H 5/12* (2013.01)

(58) Field of Classification Search
USPC ..... Plt./246
See application file for complete search history.

*Primary Examiner* — Annette H Para
(74) *Attorney, Agent, or Firm* — Samuel R. McCoy, Jr.

(57) ABSTRACT

A new and distinct *Euonymus* plant named 'HEESMIK' which is characterized by the combination of a broad spreading to upright growth habit, pale yellow juvenile foliage which is finely dotted light green, dark green, glossy mature foliage, thicker foliage which is more resistant to frost and full sun exposure, improving overall garden performance, and the stability of these characteristics from generation to generation.

3 Drawing Sheets

Latin name of the genus and species: The Latin name of the genus and species of the novel variety disclosed herein is *Euonymus japonicus.*

Variety denomination: The inventive cultivar of *Euonymus* disclosed herein has been given the variety denomination 'HEESMIK'.

CROSS REFERENCE TO RELATED APPLICATIONS

This application claims priority to the Community Plant Variety Rights application number 2016/2529, filed Oct. 18, 2016, which is herein incorporated by reference.

BACKGROUND OF THE INVENTION

Parentage: 'HEESMIK' originated as a naturally-occurring, whole plant mutation of *Euonymus japonicus* 'Heespierrolino' (U.S. Plant Pat. No. 13,852). In December of 2014 the inventor discovered the mutation at a commercial greenhouse in Rijsbergen, the Netherlands, growing amongst a cultivated population of *Euonymus japonicus* 'Heespierrolino'. The mutation was noted for its unique foliage characteristics and was subsequently isolated for further evaluation in order to confirm the distinctness and stability of the characteristics first observed. Upon confirmation of distinctness and stability, the new *Euonymus* plant was selected for commercialization and given the name 'HEESMIK'.

Asexual Reproduction: Asexual reproduction of 'HEESMIK', by way of softwood stem cuttings, was first performed in December of 2014 in Rijsbergen, the Netherlands.

Through five subsequent generations, the unique features of this cultivar have proven to be stable and true to type.

SUMMARY OF THE INVENTION

The cultivar 'HEESMIK' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HEESMIK'. These characteristics in combination distinguish 'HEESMIK' as a new and distinct *Euonymus japonicus* cultivar:

1. *Euonymus* 'HEESMIK' exhibits a broad spreading to upright growth habit with an irregular flattened globular form; and
2. *Euonymus* 'HEESMIK' exhibits pale yellow to white juvenile foliage which is finely dotted light green; and
3. *Euonymus* 'HEESMIK' exhibits light green juvenile stems which are axially striped with a lighter shade of green; and
4. *Euonymus* 'HEESMIK' exhibits light green intermediate foliage which is occasionally blotched and marbled with a lighter shade of green; and
5. *Euonymus* 'HEESMIK' exhibits dark green, glossy mature foliage; and
6. *Euonymus* 'HEESMIK' exhibits thicker foliage which is more resistant to both frost and full sun exposure, improving overall garden performance.

BOTANICAL DESCRIPTION OF THE PLANT

Figure 1:
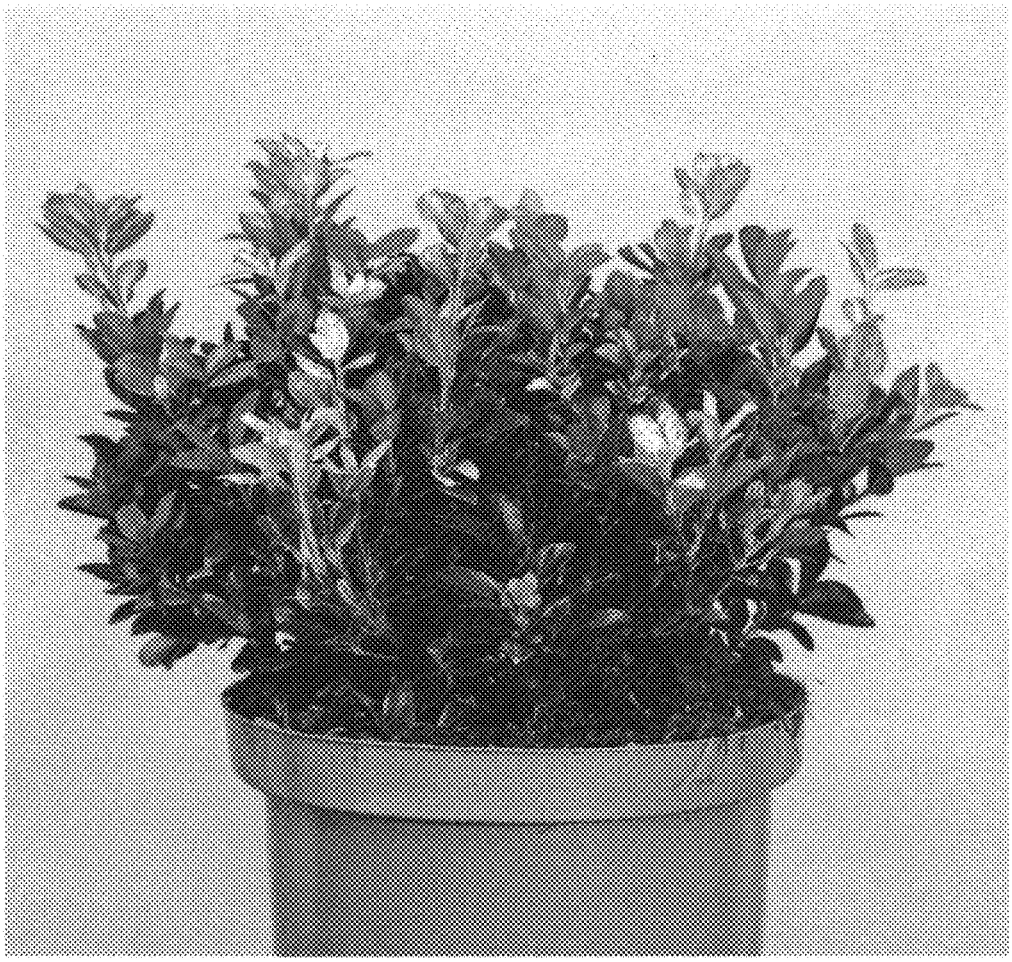
FIG. 1 illustrates, as nearly true as it is reasonably possible to make the same in color photographs of this type, an exemplary plant of 'HEESMIK' grown in Rijsbergen, the Netherlands. This plant, grown in a 25 cm nursery container, is approximately three years old from a rooted young plant.
Figure 2:
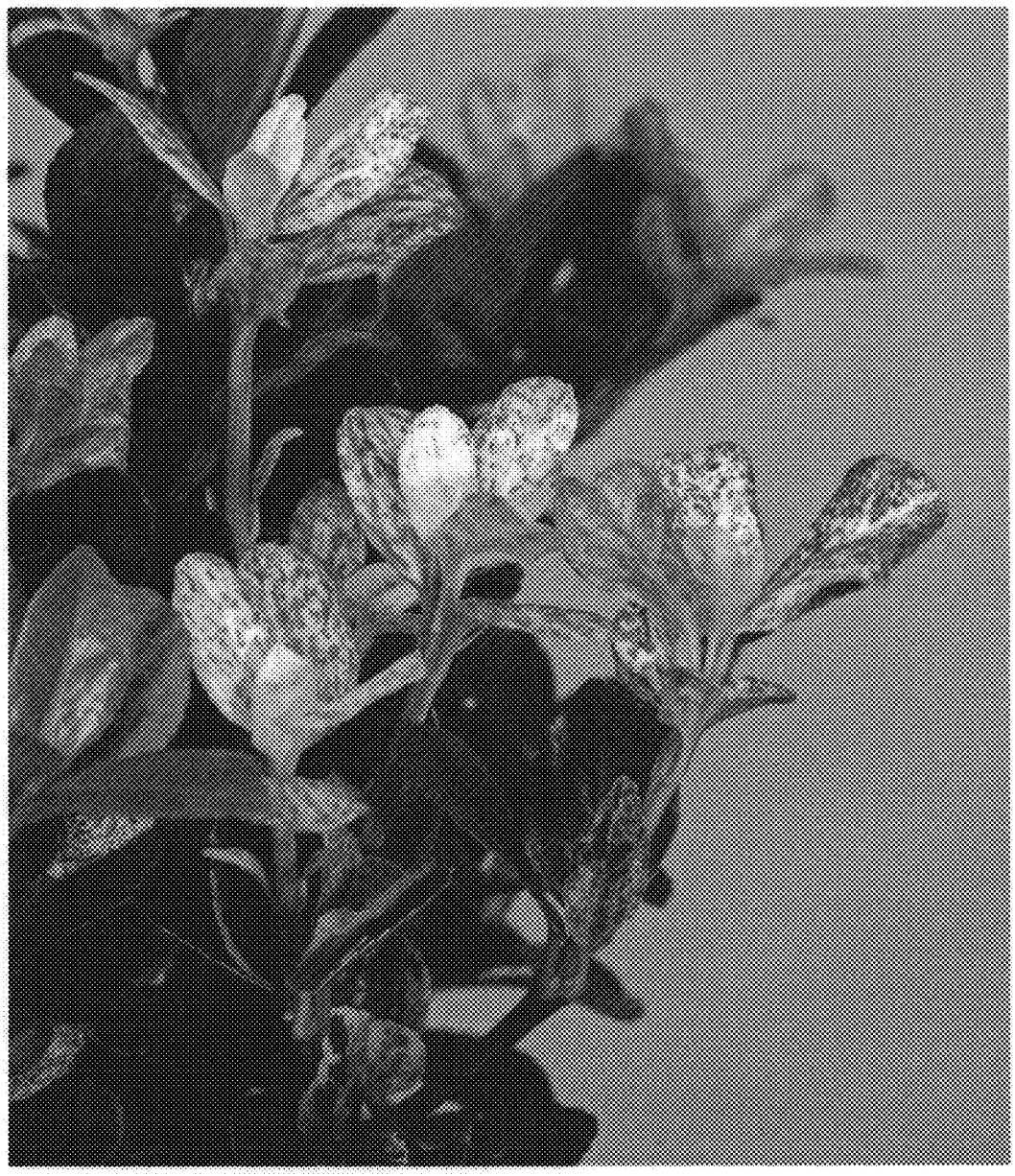
FIG. 2 illustrates, as nearly true as it is reasonably possible to make the same in color photographs of this type, the typical juvenile foliage of 'HEESMIK'.
Figure 3:
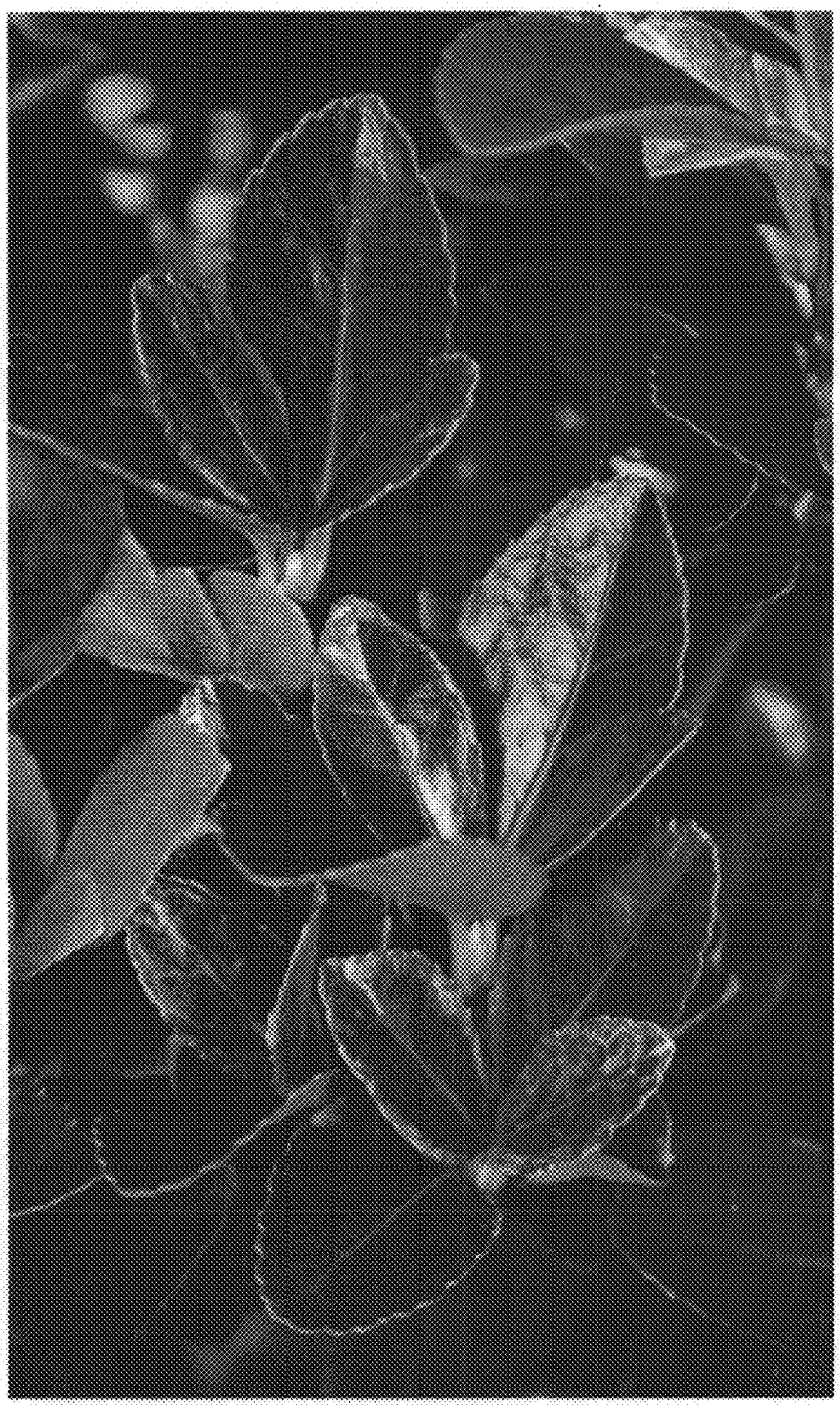
FIG. 3 illustrates, as nearly true as it is reasonably possible to make the same in color photographs of this type, the typical mature foliage of 'HEESMIK'.

The following observations and measurements, made in October of 2017, describe averages from a sample set of six specimens of three year old 'HEESMIK' plants grown in 25 cm nursery containers in Rijsbergen, the Netherlands. Plants were produced initially in a greenhouse under 50 percent shade cloth and subsequently moved outdoors with full sun exposure for finishing. Plants were maintained using overhead irrigation at regular intervals, and were fertilized as required using a slow release fertilizer. Chemical pest control measures were utilized as required.

Those skilled in the art will appreciate that certain characteristics will vary with older or, conversely, with younger plants. 'HEESMIK' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'HEESMIK' and comparisons with the parent plant and most similar commercial *Euonymus* cultivar known to the inventor are provided below.

Plant description:

*Growth habit.*—Perennial; broad spreading to upright.

*Plant form.*—Irregular flattened globular.

*Average height from base to top of foliage.*—27.9 cm.

*Average width.*—Average of 44.0 cm.

*Growth rate.*—Moderate.

*Plant vigor.*—Moderate.

*Propagation details.*—Asexual propagation is accomplished by softwood stem cuttings.

*Time to initiate roots.*—Approximately 30 days are required to initiate roots at approximately 20 to 25 degrees Celsius.

*Time to produce a marketable* 25 *cm potted plant.*—Approximately 24 months.

*Disease and pest resistance or susceptibility.*—Neither tolerance nor resistance to normal diseases and pests of *Euonymus japonicus* have been observed.

*Environmental tolerances.*—Adapt to USDA Zones 6 to 9 and temperatures as high as 40 degrees Celsius; moderate tolerance to rain; moderate to high tolerance to wind.

Root system:

*General.*—Moderately fibrous; freely branched and moderately dense rooting.

*Distribution in the soil profile.*—Shallow to moderately deep.

*Diameter, mature roots.*—0.15 cm, on average.

*Texture.*—Smooth; glabrous.

*Color.*—Greyed-yellow, RHS 161C.

Stems:

*Branching habit.*—Main stem grows from the base, freely branching with lateral branches. Pinching isn't required but will improve branching.

*Number of main stems per plant.*—15.

*Number of lateral branches per plant.*—85.

*Appearance and shape.*—Rounded.

*Length of lateral branches.*—12.7 cm.

*Diameter of lateral branches.*—Averaging 0.35.

*Internode length on lateral branches.*—2.0 cm; considerably shorter near the apex of branches, approximately 0.2 cm.

*Luster.*—Moderately glossy.

*Attitude.*—Average angle is approximately 45 degrees from vertical.

*Strength.*—Strong.

*Color, juvenile.*—Yellow-green, nearest to in between RHS 144B AND 144C; axially striped lighter, nearest to RHS 145C.

*Color, mature.*—Green, nearest to in between RHS 137A and 137B.

*Color at internodes.*—Green, nearest to in between RHS 137A and 137B.

*Color of oldest wood.*—Greyed-brown, nearest to RHS 199C.

*Pubescence.*—Glabrous.

Foliage:

*Arrangement.*—Opposite.

*Division.*—Simple.

*Attachment.*—Petiolate.

*Number of leaves per lateral branch.*—16.

*Lamina.*—Dimensions — 3.9 cm long and 2.3 cm wide, on average. Shape — Broad elliptical to elliptical. Attitude — Upward. Aspect — Slightly carinate and slightly reflexed. Apex — Obtuse. Base — Short attenuate. Margin — Crenate. Texture and luster of adaxial surface — Glabrous, coriaceous, and glossy. Texture and luster of abaxial surface — Glabrous, coriaceous, and matte. Color — Juvenile foliage, adaxial surface — In between yellow-green, RHS 150D, and white, RHS 155A; finely dotted yellow-green, nearest to a combination of RHS 144B, N144B and 145A. Juvenile foliage, abaxial surface — In between yellow-green, RHS 150D, and white, RHS 155A; finely dotted yellow-green, nearest to a combination of RHS 144B, N144B and 145A. Intermediate foliage, adaxial surface — Yellow-green, nearest to in between RHS 143B and 144A, and occasionally blotched and marbled lighter, nearest to in between RHS 144B and 144C. Intermediate foliage, abaxial surface — Yellow-green, RHS 144B. Mature foliage, adaxial surface — Nearest to in between green, RHS 139A, and greyed-green, RHS N189A, yet considerably darker. Mature foliage, abaxial surface — Yellow-green, nearest to in between RHS 146B and 147B. Venation — Pattern — Pinnate. Color, adaxial surface — Green, nearest to in between RHS 143B and 143C. Color, abaxial surface — Yellow-green, RHS 146C.

*Sheath.*—Not sheathing.

*Petiole.*—Length — 0.8 cm. Width — 0.1 cm. Texture and luster — Glabrous, smooth, and matte. Strength — Strong. Color, adaxial surface — Yellow-green, RHS 144A. Color, abaxial surface — Yellow-green, RHS 144B.

Inflorescence: To date, flowering has not been observed.
Flower buds: To date, flowering has not been observed.
Flower: To date, flowering has not been observed.
Reproductive organs: To date, flowering has not been observed.
Seed and fruit: To date, flowering has not been observed.

COMPARISONS WITH THE PARENTS

Plants of the new cultivar 'HEESMIK' differ from its parent, *Euonymus japonicus* 'Heespierrolino' (U.S. Plant Pat. No. 13,852), by the characteristics described in Chart 1.

CHART 1

| Characteristic | 'HEESMIK' | 'Heespierrolino' |
|---|---|---|
| Growth habit. | More spreading. | More upright. |
| Expression of variegation. | Variegation is most prominent in juvenile foliage, in summer. | Variegation is present in both juvenile and mature foliage, all year long. |
| General coloration of mature foliage. | Dark green. | Lighter green and occasionally variegated. |
| Plant vigor; garden performance. | More resistant to frost, and more resistant to full sun exposure. | Less resistant to frost, and susceptible to damage under full sun exposure. |

COMPARISONS WITH THE MOST SIMILAR VARIETY OF COMMON KNOWLEDGE

Plants of the new cultivar 'HEESMIK' may be distinguished from the commercial variety *Euonymus japonicus* 'LANKVELD03' (U.S. Plant Pat. No. 24,156) by the combination of characteristics described in Chart 2.

CHART 2

| Characteristic | 'HEESMIK' | 'LANKVELD03' |
|---|---|---|
| Growth habit. | More spreading. | More upright. |
| Foliage size. | Larger than 'LANKVELD03'. | Smaller than 'HEESMIK'. |
| Foliage shape. | Leaves are broader. | Leaves are more elliptical. |
| Mature foliage; general coloration. | Darker green. | Lighter green. |
| Mature foliage; luster | Glossier than 'LANKVELD03'. | Less glossy than 'HEESMIK'. |
| Growth habit. | More spreading. | More upright. |

That which is claimed is:

1. A new and distinct cultivar of *Euonymus* plant named 'HEESMIK', substantially as described and illustrated herein.

* * * * *